United States Patent
Wariar (10) Patent No.: US 8,246,563 B2
(45) Date of Patent: Aug. 21, 2012

(54) CARDIAC RHYTHM MANAGEMENT DEVICE AND SENSOR-SUITE FOR THE OPTIMAL CONTROL OF ULTRAFILTRATION AND RENAL REPLACEMENT THERAPIES

(75) Inventor: Ramesh Wariar, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1365 days.

(21) Appl. No.: 11/345,702

(22) Filed: Feb. 2, 2006

(65) Prior Publication Data

US 2007/0175827 A1    Aug. 2, 2007

(51) Int. Cl.
- *A61M 37/00*    (2006.01)
- *A61M 31/00*    (2006.01)
- *B01D 11/00*    (2006.01)
- *B01D 61/00*    (2006.01)

(52) U.S. Cl. ......... 604/4.01; 604/6.09; 604/65; 210/646

(58) Field of Classification Search ........ 604/4.01–6.16, 604/19–21; 422/44–48; 607/44, 60; 210/650, 210/134–143; 600/315
See application file for complete search history.

(56) References Cited

U.S. PATENT DOCUMENTS

| | | | |
|---|---|---|---|
| 5,938,938 A * | 8/1999 | Bosetto et al. | 210/739 |
| 6,695,790 B2 | 2/2004 | Van Oort et al. | |
| 2003/0032993 A1 * | 2/2003 | Mickle et al. | 607/60 |
| 2004/0176813 A1 * | 9/2004 | Gelfand et al. | 607/44 |
| 2006/0206029 A1 * | 9/2006 | Yair | 600/485 |
| 2007/0241915 A1 * | 10/2007 | Basson et al. | 340/576 |

OTHER PUBLICATIONS

Barnas, M. G.W., et al., "Hemodynamic Patterns and Spectral Analysis of Heart Rate Variability during Dialysis Hypotension", *J. Am Soc. Nephrol*, 10(12), (1999), 2577-2584.

Foley, R. N., et al., "Epidemiology of Cardiovascular Disease in Chronic Renal Disease", *J. Am. Soc. Nephrol*,9(12 Suppl), (1998), S16-S23.

Galetta, F., et al., "Changes in Heart Rate Variability in Chronic Uremic Patients during Ultrafiltration and Hemodialysis", *Blood Purification*, 19(4), (2001), 395-400.

Herzog, Charles A., "Cardiac arrest in dialysis patients: Approaches to alter an abysmal outcome", *Kidney International*, vol. 63, Supplement 84, (2003), S197-S200.

London, G. M., "Cardiovascular Disease in Chronic Renal Failure: Pathophysiologic Aspects", *Seminars in Dialysis*, 16(2), (Mar.-Apr. 2003), 85-94.

Prakash, S., et al., "Central, Peripheral, and Other Blood Volume Changes During Hemodialysis", *ASAIO Journal*, 48(4), (2002), 379-382.

\* cited by examiner

*Primary Examiner* — Tatyana Zalukaeva
*Assistant Examiner* — Philip R Wiest
(74) *Attorney, Agent, or Firm* — Schwegman, Lundberg & Woessner, P.A.

(57) ABSTRACT

A cardiorenal patient monitoring system comprising, either implanted or non-implanted device(s), remote peripheral device(s), computer network(s), host, and communication means between the device(s), computer network(s), and host. The preferred embodiment shows an advanced patient monitoring system for using an implanted cardiac device and a dialysis machine in renal therapy. In addition, the method of advanced patient monitoring is in conjunction with the advanced patient monitoring system is disclosed.

27 Claims, 5 Drawing Sheets

CARDIAC RHYTHM MANAGEMENT DEVICE AND SENSOR-SUITE FOR THE OPTIMAL CONTROL OF ULTRAFILTRATION AND RENAL REPLACEMENT THERAPIES

FIELD OF THE INVENTION

This invention relates to a patient management system and method of using patient physiological data measured from sensors integral to a cardiac rhythm management device to optimize ultrafiltration and/or renal replacement therapy and manage the disease state of the patient. It is also related to the treatment of congestive heart failure and fluid overload in a patient.

BACKGROUND OF THE INVENTION

Heart failure (HF) is a complex syndrome resulting from the inability of the heart to pump blood sufficient to meet the body's needs. Heart failure is a progressive disease most common in the elderly and usually caused by other diseases/conditions that gradually damage the heart such as coronary heart disease, damaged heart valves, external pressure around the heart, and cardiac muscle disease. The kidneys play an important role in compensating for the heart's inability to pump blood. Normally, healthy kidneys are responsible for various functions such as: removal of fluid and wastes, maintenance of blood pressure, maintenance of acid-base balance, stimulation of red cell production (via the release of erythropoetin), and promotion of calcium absorption. In heart failure patients, the kidneys compensate for inadequate cardiac output by increasing the volume of circulating blood (by decreasing urine output), and maintaining blood pressure. In the short term these compensatory mechanisms serve to increase cardiac performance. However in the long term they become maladaptive and lead to fluid overload in the patient, which is manifested as excess lung fluid (pulmonary edema) and dyspnea.

Thus chronic heart failure leads to a vicious cycle (termed the cardiorenal syndrome), where heart failure advances renal disease, which in turn further worsens heart failure. Chronic heart failure worsens renal diseases by several mechanisms. A reduction in the cardiac output reduces the blood flow to the kidneys and hampers the ability of the kidneys to filter wastes and remove fluid. Renal ischemia resulting from reduced oxygen availability activates the renin-angiotensin-aldosterone (RAAS) system, which causes salt and water retention and vasoconstriction (a reduction in caliber of blood vessels). Chronic activation of the RAAS system has toxic effects on the kidneys. Kidney disease in turn worsens heart failure by several mechanisms including, but not limited to, hypervolemia, increased sympathetic activity and pressure load, anemia, and inflammation. This coupled pathophysiology suggests why about 50% of patients with heart failure (i.e. 2.5 million) are estimated to have kidney disease and about 40% of patients with chronic kidney disease have heart failure. Patients suffering from failing kidneys have been reported to be the highest risk group for cardiovascular events.

Renal replacement therapy is required in patients with renal failure where the kidneys are unable to main normal functions. Renal replacement therapy is delivered using the processes of dialysis and ultrafiltration to remove the waste products, and extra fluid that accumulates when kidneys stop functioning. Renal replacement therapy also helps normalize many of the chemical imbalances that accompany kidney failure. Dialysis is the transfer of small solutes across a semi permeable membrane from the side of higher concentration (blood side) to the side of lower concentration. Ultrafiltration is the removal of water and small-to-medium solutes (by convection) through the application of a hydrostatic pressure across a semi-permeable membrane. The term "clearance" is used to describe the complete removal of a substance from a specific volume of blood per unit time.

Extracorporeal renal replacement therapy (ERRT) is the most common type of renal therapy where blood is circulated outside the body through a filter called a hemodialyzer. Most patients need three or four therapy sessions per week, each lasting two to four hours. During dialysis small solutes are removed by diffusion, the concentration of solutes in the plasma decreases, and clearance is obtained. Ultrafiltration can be combined with dialysis to remove both fluid and small solutes from the blood plasma during ERRT. It is important to measure the amount of clearance and fluid removed during dialysis. Hemofiltration is the combination of ultrafiltration and fluid replacement.

Blood circulation for ERRT is provided using an electromechanical system that comprises a blood pump to move blood from the patient's artery/vein through an extracorporeal blood circuit containing tubes and a hemofilter or hemodialyzer. For hemodialysis an ionic solution called the dialysate is pumped through the dialyzer in a direction counter-current to blood flow and on the opposite side of the semi permeable membrane. Because the dialysate does not contain wastes (such as urea and creatinine) that are present in blood, the chemical concentration gradient of these substances across the semi-permeable membrane drives diffusion in to the dialysate stream, which is discarded. The dialysis instrument also controls the transmembrane pressure to ensure that the required fluid is removed by ultrafiltration during the therapy. If necessary, small amounts of fluids and medications may be injected into blood returning to the patient. During ultrafiltration therapy, since dialysis is not required a dialysate solution is not needed, and blood is passed through a hemofilter across which a fluid similar to plasma is filtered. Depending on the permeability of the membrane, a filtrate similar to plasma is collected through a filtrate tube and temporarily stored in a filtrate bag. Through convection, the filtered fluid also drags solutes of different sizes and molecular weights across the membrane.

Due to the cardiorenal syndrome, patients with advanced heart failure are often fluid overloaded. Because patients still retain kidney function, they are treated using a class of drugs called diuretics that promote urine discharge. However diuretics are known to have adverse events. Sometimes patients may be admitted to the hospital for decompensated heart failure and require therapies such as ultrafiltration for immediate fluid removal. Ultrafiltration, which is typically used for renal therapies, is thus being increasingly used for managing fluid removal from heart failure patients. The advantages of ultrafiltration over diuretics are that the rate of fluid output can be easily adjusted, and the process removes both sodium and water, which is important to maintain fluid balance.

An increasing number of heart failure patients are also implanted with cardiac rhythm management (CRM) devices that treat their heart failure condition. CRM devices such as pacemakers, implantable cardioverter defibrillators (ICDs), and cardiac resynchronization therapy (CRT) devices are used to treat electrical conduction disorders of the heart. Also CRM devices are equipped with a variety of implanted sensors that monitor the heart and provide for the measurement of several physiological parameters, including, but not limited to, electrical cardiac activity, heart rate, heart rate variability, autonomic balance, patient activity, temperature, thoracic fluid, and respiration. These sensors are advantageous over external sensors because they can make measurements automatically in the ambulatory patient while minimizing patient discomfort and the need for patient compliance. About 60% of cardiovascular deaths in patients undergoing renal therapy are thought to be due to sudden cardiac death making patients undergoing end-stage renal therapies, such as dialysis, potential candidates for CRM devices.

It is beneficial to measure the physiological characteristics of the body during renal replacement therapy, or ultrafiltration for heart failure. Present methods of renal replacement therapy do not provide a means whereby implanted sensor measurements may be taken. For example during renal replacement or ultrafiltration therapies, an excess removal of fluid from the patient can lead to a rapid reduction in blood pressure (hypotension). This occurs due to the inability of the body to increase total peripheral resistance in the face of decreasing cardiac output. Thus a method is required to continuously monitor the fluid status and the autonomic function of the patient and control ultrafiltration rate in order to ensure that the patient reaches his/her dry weight without hypotensive episodes. Sensors present in implanted CRM devices can be used to monitor the patient during ERRT and/or ultrafiltration therapies and control therapy. Autonomic balance can be measured from heart rate variability using cardiac electrical activity measured from CRM devices, which could be used to detect increasing sympathetic tone prior to a hypotensive episode. Similarly the patient's thoracic fluid status measured using thoracic impedance in CRM devices may be useful in determining the fluid state of the patient. Also blood conductivity measurements from implanted CRM devices may be used for hematocrit determination, and dialysis clearance calculations of sodium, which is used as a surrogate for urea.

In addition to the above measurements that are made during ERRT or ultrafiltration, chronic implanted sensor data collected between treatments (e.g. autonomic balance, thoracic fluid status) in dialysis patients can be captured in the advanced patient management (APM) system and used by the caregiver to better manage the patient. For example chronic data from the CRM device and the APM system at home can be used to determine the rate of fluid build-up between dialysis sessions and alert the need for ERRT.

Presently the caregiver is required to analyze the data and provide predictive and post-event diagnosis based on the data. However, as the amount of data collected regarding a particular patient increases, it becomes more difficult for a caregiver to assimilate and provide a meaningful analysis of all of the data. In addition, it is difficult for a caregiver to identify trends and other information from particular patients and leverage this knowledge for the treatment of larger populations. Thus by integrating CRM sensors and the advanced patient management system with renal/ultrafiltration therapies, the patient can be more optimally managed.

Generally, during renal replacement therapy, the physiological characteristics of a patient are measured externally. Such externally measured physiological characteristics are not as beneficial as physiological characteristics that are measured internally by an implanted device. There is a need for a process whereby the local measurements of the physiological characteristics of a patient can be used in renal therapy and in the health management of patients with cardiac and renal disease.

SUMMARY

The present invention is an integrated cardiac and renal disease management system that comprises a renal therapy device and at least one implanted cardiac rhythm management (CRM) device configured to communicate with the renal therapy device. The renal therapy device includes devices for extracorporeal renal replacement therapies as well as ultrafiltration therapy for heart failure. The implanted CRM device includes sensors for measuring patient physiological parameters. Today CRM devices allow the measurement of several physiological parameters e.g. heart rate, heart rate variability, autonomic balance, heart vibrations, intracardiac pressure, thoracic fluid status, respiration, and patient activity level. In the future other measurements may be possible such as temperature, pH, oxygenation, cardiac volumes, blood pressure, and ejection fraction. The measured physiological parameters are transmitted to the renal therapy device that is configured to modify renal therapy applied to a patient in response to the patient physiological parameters received. Renal therapy is modified by at least controlling the flow of fluid into or out of the renal therapy device providing dialysis and/or ultrafiltration therapy. The renal disease therapy management system also provides a method of managing therapy applied to patients suffering from renal disease by including implanted sensor measurements, and remote patient care devices that measure blood pressure and weight. Similarly information from renal therapy devices such as ultrafiltrate conductivity and hematocrit may be transmitted to the CRM device or APM system and used for managing the HF status of the patient. Data representative of patient blood pressure, weight and other patient physiological parameters captured by the implanted CRM device and external sensors, and the renal therapy device are transmitted to a patient management host system where a patient care provider can monitor patient physiological parameters and modify renal therapy based on patient health data received.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

GENERAL DESCRIPTION

The present system and methods are described with respect to an advanced patient management system configured to collect patient-specific information, store and collate the information, and generate actionable recommendations for better managing the renal and cardiac disease of the patient. The advanced patient management system is also configured to leverage a remote communications infrastructure to provide automatic CRM device follow-ups, to collect data, coordinate therapy, and to determine if remote devices are functioning properly. The term "patient" is used herein to mean any individual from whom information is collected. The term "caregiver" is used herein to mean any provider of services, such as health care providers including, but not limited to, nurses, doctors, and other health care provider staff.

Figure 1:
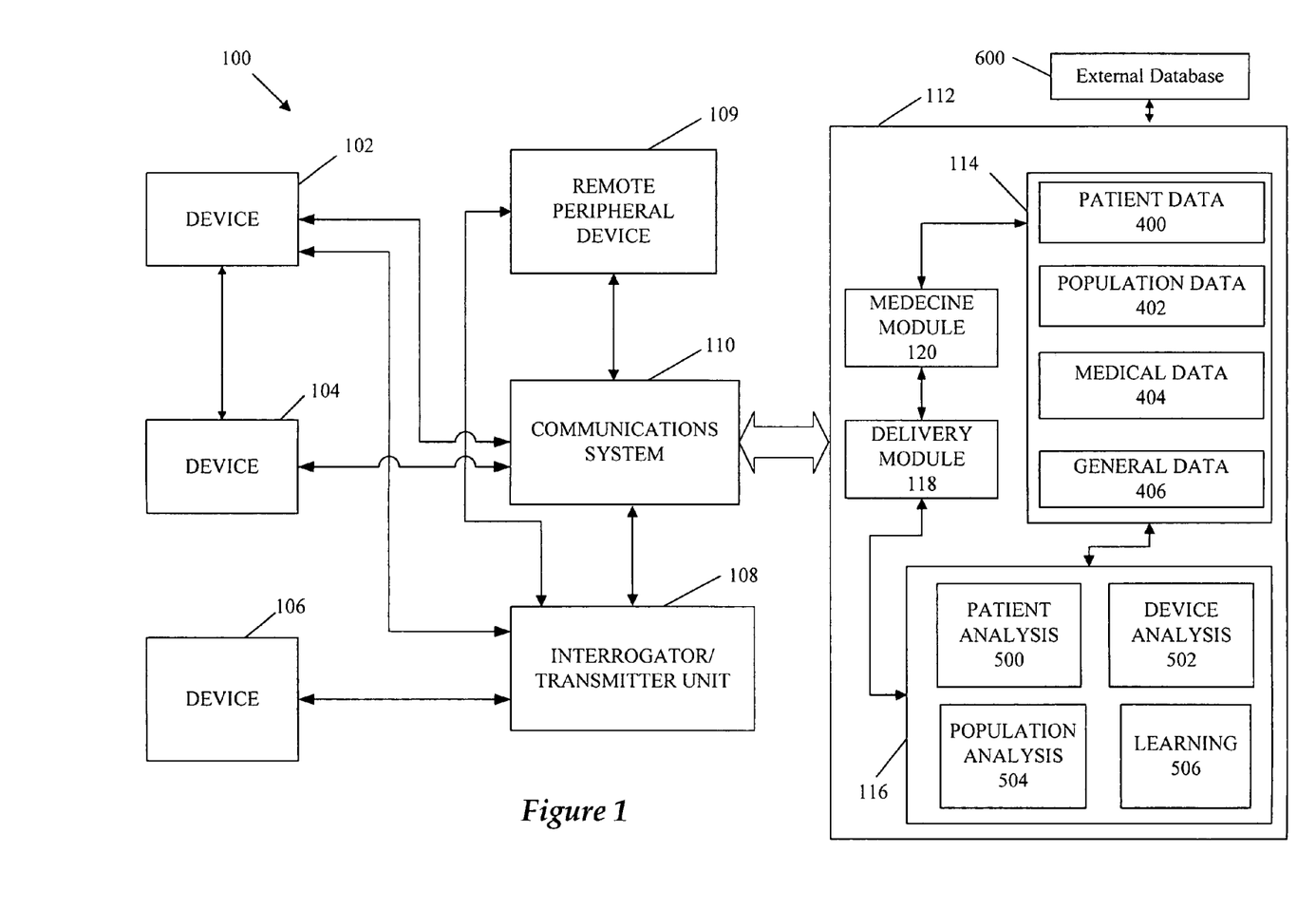
FIG. 1 is an example advanced patient management system made in accordance with the present invention.

FIG. 1 illustrates an example advanced patient management system 100 made in accordance with the present invention. Advanced patient management system 100 generally includes the following components: one or more devices 102, 104, and 106, one or more interrogator/transceiver units 108, a communication system 110, one or more remote peripheral devices 109, and a host 112.

Each component of the advanced patient management system 100 can communicate using the communication system 110. Some components may also communicate directly with one another. For example, devices 102 and 104 may be configured to communicate directly with one another. The various components of the example advanced patient management system 100 illustrated herein are described below. Further, the advanced patient management system 100 may utilize other implantable devices as well that provide physiological measurements of the patient, such as drug pumps, neurological devices (e.g., stimulators), oxygen sensors, etc.

Devices 102, 104, and 106 can be devices that are implanted in the human body or external devices that are not implanted in the human body, all of which are used to measure patient physiological data. Such devices include a multitude of devices to measure data relating to the human body, such as temperature (e.g., a thermometer), blood pressure (e.g., a sphygmomanometer), blood characteristics (e.g., glucose levels), body weight, physical strength, mental acuity, diet, heart characteristics, and relative geographic position (e.g., a Global Positioning System (GPS)).

Figure 2:
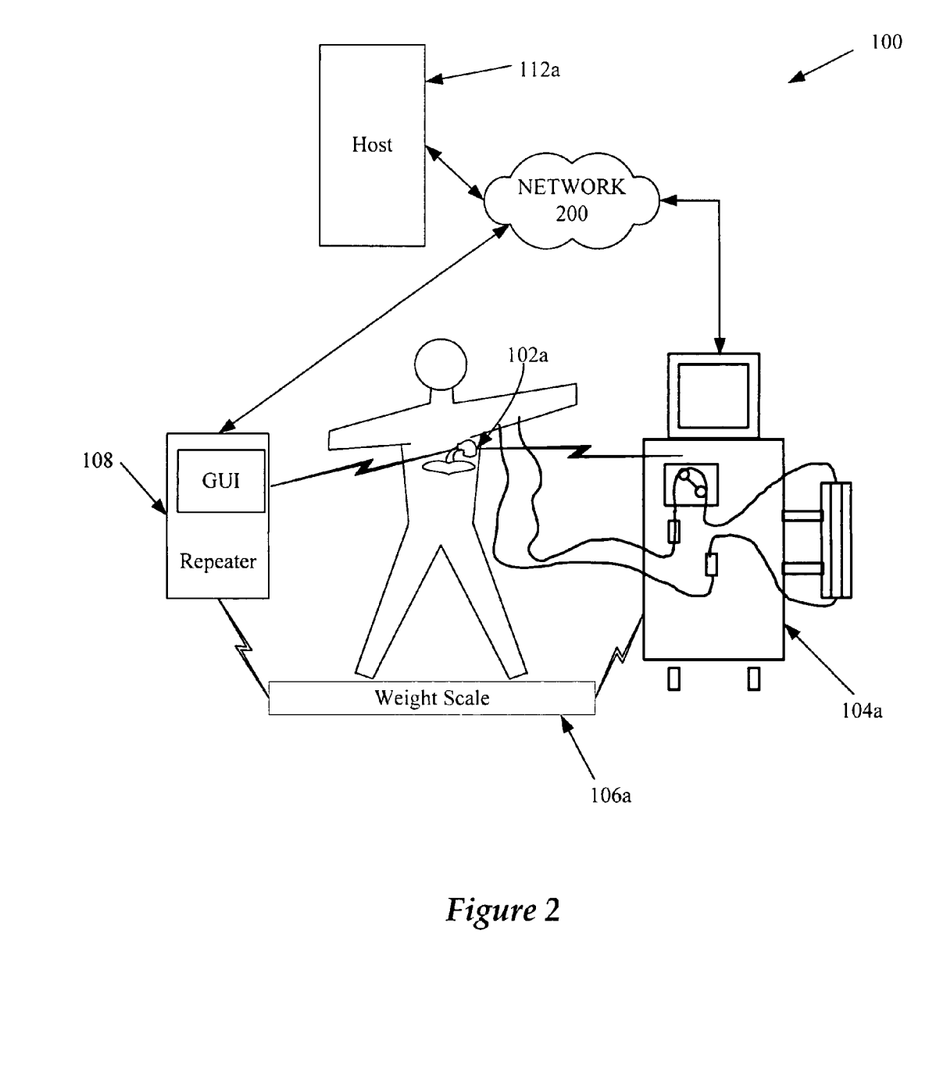
FIG. 2 illustrates an example of an advanced patient management system for used during renal therapy.

In the present embodiment, illustrated in FIG. 2, device 102 is a device implanted in the human body, preferably a cardiac rhythm management (CRM) device 102a. Devices 104 and 106a are external devices. Device 104a is a renal therapy device and device 106a is a patient weight scale. The renal therapy device 104a is a mechanical device that performs ultrafiltration and/or dialysis. The implanted CRM device 102a is configured to communicate via radio frequency to the renal therapy device 104a directly, or through a repeater 108. Transmission of patient physiological data from the CRM device 102a to the renal therapy device 104a allows the physiological parameters transmitted to be viewed on a screen of the renal therapy device 104a and used by the dialysis caregiver to modify therapy. It is contemplated that the renal therapy device 104a is located in one embodiment at the caregiver's office or hospital, and in an alternative embodiment the renal therapy device 104a is located at the home of the patient and configured to allow the patient to perform renal therapy on himself or herself, without the assistance of a caregiver.

The implanted CRM device 102a includes sensors for measuring a patient's physiological parameters including, but not limited to, heart rate, heart rate variability, autonomic balance, heart vibrations, intracardiac pressure, thoracic fluid status, respiration, patient activity level, pH, oxygenation, cardiac volumes, blood pressure, and ejection fraction. The patient's physiological parameters captured are transmitted to the renal therapy device 104a are used to modify and optimally control the dialysis and or ultrafiltration therapy being applied to a patient in order to prevent intracardiac hypotension. Hypotension is a result of a drop in blood pressure produced by a reduction of intravascular volume, and the inability of the autonomic system to compensate by increasing total peripheral resistance. As an example, bioimpedance monitors that are integral to a CRM device 102a can be used to measure a number of physiologically relevant variables. Accordingly, renal therapy is modified by at least controlling the flow of fluid into or out of the renal therapy device 104a while providing dialysis and ultrafiltration therapy.

When a patient is receiving renal therapy from device 104a, the patient's physiological parameters measured during renal therapy, such as blood pump flow, dialysate flow (if applicable), dialysate conductivity (if applicable), hematocrit, arterial pressure, venous pressure, and blood plasma conductivity, along with changes in heart rate, heart rate variability, thoracic fluid status, and cardiac stroke volume that are measured by the CRM device 102a can be transmitted to the host system 112a where such data is trended to determine cardiac performance changes with ultrafiltration and dialysis. Host system 112a may also process patient physiological data, such as heart rate variability, to estimate and trend patient sympathetic balance in order to predict a sympathetic withdrawal and hypotension. Host system 112a may also process patient physiological parameters measured during renal therapy to enhance cardiovascular care. The autonomic withdrawal may be monitored from signal processing of heart rate variability. Using these parameters, patient-specific thresholds for hypotension and ultrafiltration profiles could be determined to minimize hypotensive episodes.

Referring back to FIG. 1, when a patient is not receiving therapy from device 104, continuous ambulatory measurements using implanted sensor measurements, and other external measurements of patient blood pressure and weight may be captured and transmitted with devices 102 and 108 to a database within the host system 112 along with patient intrathoracic impedance measured with the implanted device 102. Using intrathoracic impedance, the volume of fluid in the central compartment (i.e. heart and lungs) could be continuously monitored during dialysis or other therapy and used for hypotension prediction, fluid overload monitoring, and other medical conditions. In addition, continuous ambulatory measurements could be transmitted to the host system 112 where such measurements are stored and can be retrieved by the physician/nurse to appropriately tailor patient therapy.

Patients with advanced heart failure and/or receiving renal therapy are often chronically fluid overloaded because of the difficulty of determining the patient's euvolomic state or "dry weight". Measurements recorded by an implanted medical device 102 of intracardiac pressures using implanted sensors, bioimpedance measurements of central fluid volumes (via intrathoracic impedance), accelerometer heart sounds and patient weight changes (potentially with leg-to-leg bioimpedance) are used to monitor changes in a patient's weight, and the presence of peripheral edema. These measurements are processed by a control system within the mechanical device 104 that performs renal therapy in order to tailor fluid removal during therapy in order to keep the patient at a euvolemic state.

It is also contemplated that the sensors within CRM device 102a, include temperature, ultrasound, and conductivity. The patient physiological measurements recorded by these sensors may be combined with the unique features of renal therapy (e.g. ability to change blood temperature, hematocrit and/or ionic concentrations) to improve renal therapy. CRM devices that include ultrasound sensors can be used to measure blood density (that are related to changes in blood hematocrit and total plasma protein), which in turn could be used to control changes in intravascular fluid volume by adjusting ultrafiltration during dialysis. Alternatively, certain variables measured during dialysis (e.g. blood conductivity) could be used to adjust parameters of the CRM device.

DETAILED DESCRIPTION

I. Devices

Referring to FIG. 1, devices 102, 104, and 106 can be implantable devices or external devices that may provide one or more of the following functions with respect to a patient: (1) sensing, (2) data analysis, and (3) therapy. For example, in one embodiment, devices 102, 104, and 106 are either implanted or external devices used to measure a variety of physiological, subjective, and environmental conditions of a patient using electrical, mechanical, and/or chemical means. The devices 102, 104, and 106 can be configured to automatically gather data or can require manual intervention by the patient or caregiver. The devices 102, 104, and 106 can be configured to store data related to the physiological and/or subjective measurements and/or transmit the data to the communication system 110 using a variety of methods, described in detail below. Although three devices 102, 104, and 106 are illustrated in the example embodiment shown, more or fewer devices may be used for a given patient.

The devices 102, 104, and 106 can be configured to analyze the measured data and act upon the analyzed data. For example, the devices 102, 104, and 106 are configured to modify therapy or provide alarm indications based on the analysis of the data.

In one embodiment, device 102 is an implantable cardiac rhythm management (CRM) device 102a and device 104 is a renal therapy device 104a. The physiological measurements recorded by the CRM device 102a are transmitted to the renal therapy device 104a, which processes data representative of patient physiological parameters and modifies the renal therapy the patient receives in response to the data representative of patient physiological parameters.

In other embodiments, devices 102, 104, and 106 also provide therapy. Therapy can be provided automatically or in response to an external communication. Devices 102, 104, and 106 are programmable in that sensing characteristics during therapy (e.g., duration and interval), or communications can be altered via communication between the devices 102, 104, and 106 and other components of the advanced patient management system 100. Devices 102, 104, and 106 can also perform self-diagnostics or be interrogated by the communication system 110 to verify that the devices are functioning properly. Examples of different embodiments of the devices 102, 104, and 106 are provided below.

Devices implanted within the body have the ability to sense and communicate as well as to provide therapy. Implantable devices can provide direct measurement of characteristics of the body including, but not limited to and without limitation, electrical cardiac activity (e.g., a pacemaker, cardiac resynchronization management device, defibrillator, etc.), physical motion, temperature, heart rate, activity, blood pressure, breathing patterns, cardiac volumes, ejection fractions, blood viscosity, blood chemistry, blood glucose levels, and other patient-specific clinical physiological parameters, while minimizing the need for patient compliance.

A heart rhythm sensor, typically found in a pacemaker or defibrillator, is one example of an implanted device sensor. In the heart, an electrical wave activates the heart muscle just prior to contraction. As is known in the art, implanted electrical circuits and lead-wires transduce the heart's activation event and reject other, non-essential electrical events. By measuring the time interval between activation events, the heart rhythm can be determined. A transthoracic impedance sensor is another example of a sensor in an implanted device sensor. During the respiratory cycle, large volumes of air pass into and out of the body. The electrical resistance of the thorax changes markedly as a result of large differences in conductivity of air and body tissues. The thoracic resistance can be measured during respiration and converted into a measurable electrical signal (i.e., impedance) so that breathing rate and profile can be approximated. Implantable devices can also sense chemical conditions, such as glucose levels, blood oxygen levels, etc. Further, the advanced patient management system 100 may utilize other implantable devices as well that provide physiological measurements of the patient, such as drug pumps, neurological devices (e.g., stimulators), oxygen sensors, etc.

Derived measurements can also be determined from the implantable device sensors. For example, a sleep sensor can rely on measurements taken by an implanted impedance sensor that measures respiration, and the accelerometer that measures body activity levels. The sleep sensor can estimate sleeping patterns based on the measured activity levels. Other derived measurements include, but are not limited to, a functional capacity indicator, autonomic tone indicator, sleep quality indicator, cough indicator, anxiety indicator, and cardiovascular wellness indicator for calculating a quality of life indicator quantifying a patient's overall health and well-being.

Devices 102, 104, and 106 can be devices that are implanted in the human body or external devices that are not implanted in the human body, all of which are used to measure patient physiological data. Devices 102, 104, and 106 can also be environmental sensors. The devices can be placed in a variety of geographic locations (in close proximity to patient or distributed throughout a population) and record non-patient specific characteristics such as, but not limited to, temperature, air quality, humidity, carbon monoxide level, oxygen level, barometric pressure, light intensity, and sound.

One or more of the devices 102, 104, and 106 (for example, device 106) may be external devices that measure subjective or perceptive data from the patient. Subjective data is information related to a patient's feelings, perceptions, and/or opinions, as opposed to objective physiological data. For example, the "subjective" devices can measure patient responses to inquiries such as "How do you feel?" and "How is your pain?" The device can prompt the patient and record subjective data from the patient using visual and/or audible cues. For example, the patient can press coded response buttons or type an appropriate response on a keypad. Alternatively, allowing the patient to speak into a microphone and using speech recognition software to process the subjective data may be collected. Notwithstanding, in the present embodiment, device 106 is a weight scale 106a as illustrated in FIG. 2.

In one example embodiment, the subjective device presents the patient with a relatively small number of responses to each question posed to the patient. For example, the responses available to the patient may include three faces representing feelings of happiness, nominalness, and sadness. Averaged over time, a trend of a patient's well being will emerge with a finer resolution than the quanta of the three responses.

The subjective data can be collected from the patient at set times, or, alternatively, collected whenever the patient feels like providing subjective data. The subjective data can also be collected substantially contemporaneously with physiological data to provide greater insight into overall patient wellness. The subjective device 106 can be any device that accepts input from a patient or other concerned individual and/or provides information in a format that is recognizable to the patient. Device 106 typically includes a keypad, mouse, display, handheld device, interactive TV, cellular telephone or other radio frequency ("RF") communications device, cordless phone, corded phone, speaker, microphone, email message, or physical stimulus.

The advanced patient management system 100 may also include one or more remote peripheral devices 109. The remote peripheral device 109 may include, for example and without limitation, cellular telephones, pagers, personal digital assistant (PDA) devices, facsimiles, remote computers, printers, video and/or audio devices, etc. The remote peripheral device 109 can communicate using wired or wireless technologies and may be used by the patient or caregiver to communicate with the communication system 110 and/or the host 112. For example, the remote peripheral device 109 can be used by the caregiver to receive alerts from the host 112 based on data collected from the patient and to send instructions from the caregiver to either the patient or other clinical staff. In another example, the remote peripheral device 109 is used by the patient to receive periodic or real time updates and alerts regarding the patient's health and well-being.

II. Interrogator/Transceiver Unit

Figure 4:
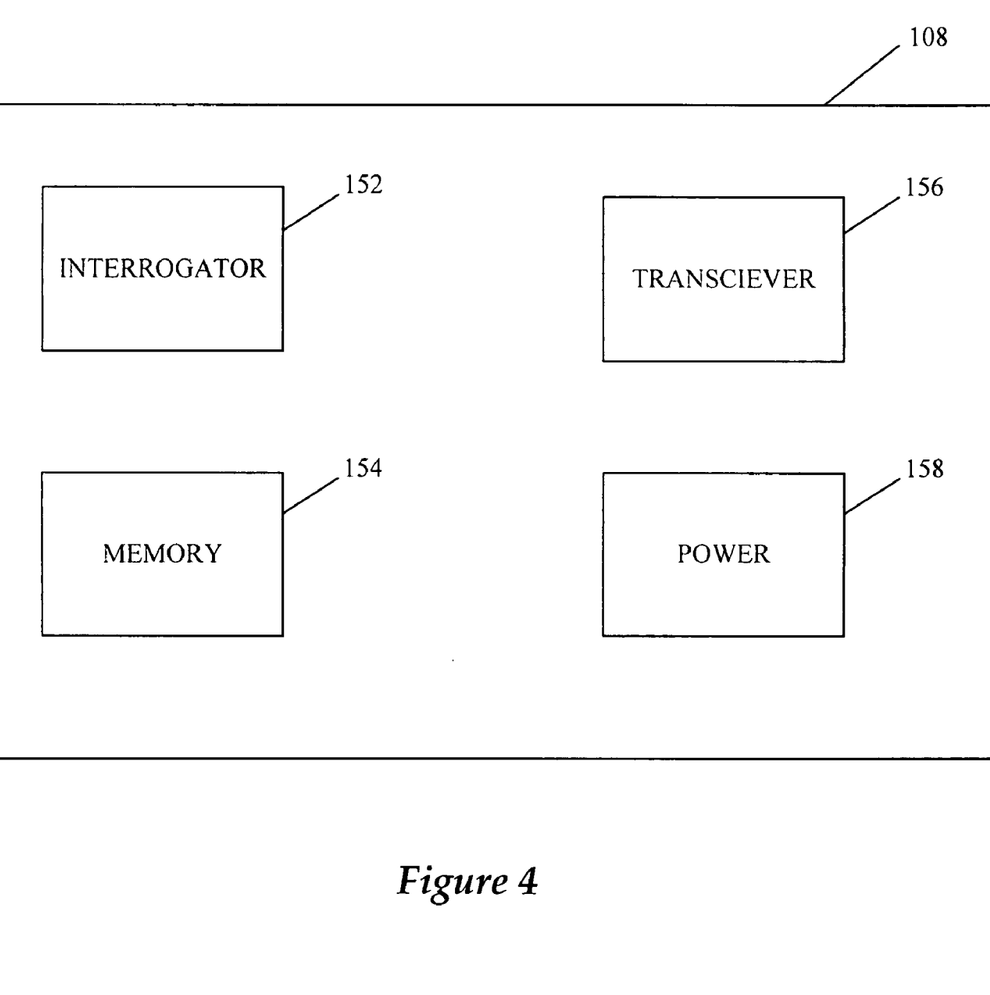
FIG. 4 illustrates an example interrogator/transceiver unit made in accordance with the present invention.

Referring now to FIG. 4, the example advanced patient management system 100 includes one or more interrogator/transceiver units (ITUs), such as ITU 108. The ITU 108 includes an interrogator module 152 for sending and receiving data from a device, such as devices 102, 104, and 106, a memory module 154 for storing data, and a transceiver module 156 for sending and receiving data to and from other components of the advanced patient management system 100. The transceiver module may also operate as an interrogator of the devices 102, 104 and 106. The ITU 108 also includes a power module 158 that provides power.

The ITU 108 may perform one or more of the following functions: (1) data storage; (2) data analysis; (3) data forwarding; (4) patient interaction; (5) patient feedback; and (6) data communications. For example, the ITU 108 may facilitate communications between the devices 102, 104, and 106 and the communication system 110. The ITU 108 can, periodically or in real-time, interrogate and download into memory clinically relevant patient data from the devices 102, 104, and/or 106. This data includes, in the cardiac sensor context, for example, P and R-wave measurements, pacing, shocking events, lead impedances, pacing thresholds, battery voltage, capacitor charge times, ATR episodes with electrograms, tachycardia episodes with electrograms, histogram information, and any other clinical information necessary to ensure patient health and proper device function. The ITU 108 could also store data from the renal therapy device 104*a* such as patient weight (prior to therapy), blood pump speed, ultrafiltration rate, hematocrit, ultrafiltrate conductivity, ultrafiltrate and blood temperature etc. In the present embodiment, the data is sent to the ITU 108 by device 102 real-time or periodically uploaded from buffers in the device.

The ITU 108 may also allow patient interaction. For example, the ITU 108 may include a patient interface and allow the patient to input subjective data. In addition, the ITU 108 may provide feedback to the patient based on the data that has been analyzed or based on information communicated by the communication system 110.

In another embodiment, the ITU 108 includes a telemetry link from the devices to a network that forms the basis of a wireless LAN in the patient's home. The ITU 108 systematically uploads information from the devices 102, 104, and/or 106 while the patient is sleeping, for example. The uploaded data is transmitted through the communication system 110 or directly to the host 112. In addition, in one embodiment the ITU 108 functions in a hybrid form, utilizing wireless communication when available and defaulting to a local wireless portal or a wired connection when the wireless communication becomes unavailable.

Some devices, such as legacy implanted CRM devices, communicate via an internal telemetry transceiver that communicates with an external programmer. The communication range of such devices is typically 1 to 4 inches. ITU 108 may include a special short-range interrogator that communicates with a legacy device.

When the interrogator 152 uses radio frequency to communicate with the devices 102, 104, 106, the ITU 108 may be in the form of a small device that is placed in an inconspicuous place within the patient's residence or in the hospital. Alternatively, the ITU 108 may be implemented as part of a commonly used appliance in the patient's residence or hospital. For example, the ITU 108 may be integrated with an alarm clock that is positioned near the patient's bed. In another embodiment, the ITU 108 may be implemented as part of the patient's personal computer system. One of average skill in the art can easily foresee that other embodiments are also possible.

In another embodiment, the ITU 108 may comprise a handheld device such as a PDA, cellular telephone, or other similar device that is in wireless communication with the devices 102, 104, and 106. The hand-held device may upload the data to the communication system 110 wirelessly. Alternatively, the hand-held device may periodically be placed in a cradle or other similar device that is configured to transmit the data to the communication system 110.

In one embodiment, the ITU 108 can perform analysis on the data and provide immediate feedback, as well as perform a variety of self-diagnostic tests to verify that it is functioning properly and that communication with the communication system 110 has not been compromised. For example, the ITU 108 can perform a diagnostic loop-back test at a set time either by the host 112 or healthcare provider, which involves sending a request through the communication system 110 to the host 112. The host 112 can then reply with a response back through the communication system 110 to the ITU 108. If a specific duration elapses before the ITU 108 receives the response or the ITU 108 receives an unexpected response, or if the host 112 does not receive the diagnostic test communication, the ITU 108 can provide indications that the system is not functioning properly and the host 112 can alert an operator that there may be compromised communications or other malfunctions with that specific ITU 108.

For example, if wireless communications between the ITU 108 and the communication system 110 have been interrupted, and the ITU 108 performs a self-diagnostic test that fails, the ITU 108 may alert the patient so that corrective action may be taken. The alert can take the form of a sound or a visual and/or audible enunciator to alert the patient that communication has been interrupted. In another embodiment, the ITU 108 can automatically fail-back to a wired system to communicate with the communication system 110 and perform the same communications compromise checks.

In other embodiments of the advanced patient management system 100, the ITU 108 function can be integrated into devices 102, 104, and 106, so that the devices can communicate directly with the communication system 110 and/or host 112. The devices 102, 104 and 106 can incorporate multimode wireless telecommunications, including, but not limited to, cellular, BLUETOOTH, or IEEE 802.11B to communicate with the communication system 110 directly or through a local wireless to wired portal in the patients' home. This communication, while not required, may be encrypted for patient privacy or other reasons. For example, device 102 may include a miniature cellular phone capable of wirelessly uploading clinical data from the device on a periodic basis. This is particularly advantageous for devices that are mobile (e.g., an implanted device in a patient that is traveling).

To conserve the energy of the devices 102, 104, and 106, particularly when the devices (e.g., device 102) are configured to communicate directly with the communication system 110 without using an ITU 108, in one example embodiment the devices are configured to communicate during a given duty cycle. For example, the device 102 can be configured to communicate with the communication system 110 at given intervals, such as once a week. The device 102 can record data for the time period (e.g., a week) and transmit the data to the communication system 110 during the portion of the cycle that transmission is active and then conserve energy for the rest of the cycle. In another example, the device 102 conserves energy and only communicates with the communication system 110 when an "interesting" event, including, but not limited to, a heart arrhythmia, has occurred. In this manner, device 102 can communicate directly with the communication system 110 and/or host 112 without requiring an ITU 108, while conserving the energy of the device by communicating only during a given duty cycle.

The interrogation rate of the ITU 108 can be varied depending on disease state and other relevant factors. In addition, the devices 102, and 104 can be configured to "wake up" frequently (e.g., once every couple minutes) to provide the ITU 108 an access window for the ITU 108 to provide commands to the devices 102, 104, and 106, as well as upload data from the devices.

If multiple devices, such as devices 102, 104, and 106, are provided for a given patient, each device may include its own means for communicating with the ITU 108 or communication system 110. Alternatively, a single telemetry system may be implemented as part of one of the devices, or separate from the devices, and each device 102, 104, and 106 can use this single telemetry system to communication with the ITU 108 or the communication system 110.

In yet another embodiment, the devices 102, 104, and 106 include wires or leads extending from devices 102, 104, and 106 to an area external of the patient to provide a direct physical connection. The external leads can be connected, for example, to the ITU 108 or a similar device to provide communications between the devices 102, 104, and 106 and the other components of the advanced patient management system 100. Furthermore the leads extending from devices 102, 104, and 106 may allow the patient to connect to other communication devices, including but not limited to, cell phones or land lines to facilitate communication with the host 112, or other caregivers while traveling.

The advanced patient management system 100 can also involve a hybrid use of the ITU 108. For example, the devices 102, 104, and 106 can intelligently communicate via short-range telemetry with the ITU 108 when the patient is located within the patient's home and communicate directly with the communication system 110 or host 112 when the patient is traveling. This may be advantageous, for example, to conserve battery power when the devices are located near an ITU 108.

In a preferred embodiment, device 104 is a renal therapy device 104a that communicates with at least one implanted device 102 and an interrogator/transceiver unit 108, a communications system 110, one or more remote peripheral devices 109, and a host system 112. The renal therapy device 104a provides a method for real-time interpretation of patient physiological parameters received from an implanted medical device 102 during renal therapy. The patient's physiological data received is processed by a renal therapy device control system and manipulates renal therapy a patient receives in direct response to the patient physiological data processed. During use of the renal therapy device 104a on a patient, the device illustrates via visual and auditory notification of when patient physiological parameters are outside of an acceptable range and automatically modifies the therapy being administered to the patient. The visual and auditory notification and illustrations include a visual illustration of the changes made to the various therapies capable of being provided to the patient in the form of a message displayed on a display, or a flashing LED. The auditory notification of when patient's physiological parameters are outside of an acceptable range may be in the form of a beeping, buzzing or vibrating alarm that continues until the patient's physiological parameters are stabilized or the alarm is silenced by a caregiver. The renal therapy control system further includes a communicator that provides the renal therapy device 104a with a means for transmitting to and receiving communications from the communications system 110 and/or the host system 112 and a means for transmitting to and receiving communications from devices 102, and 106. In one embodiment, device 102 is an implanted CRM device 102a that communicates with the renal therapy devise 104a directly or indirectly via CRM device 102a communication with the host system 112.

Figure 3:
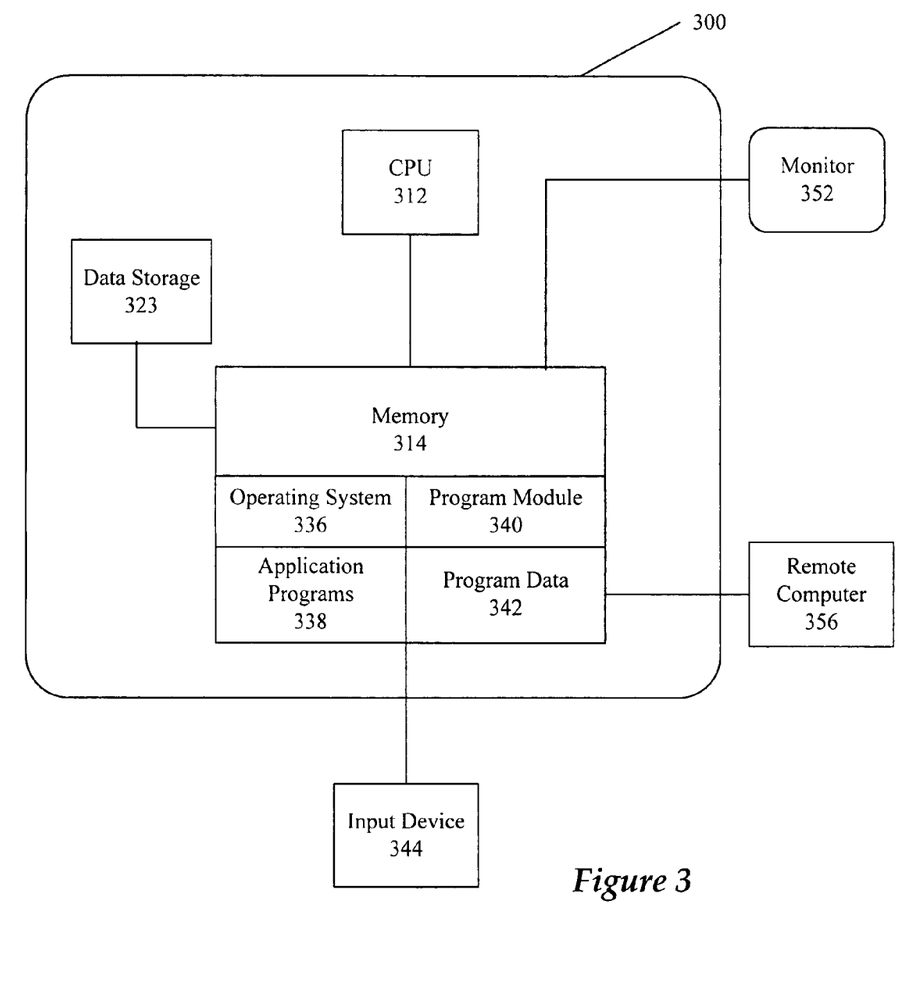
FIG. 3 illustrates an example interrogator/transceiver unit made in accordance with the present invention.

The renal therapy device 104a communications and control system, illustrated in FIG. 3, includes an input device, 344, for manual input of data, a central processor 312, memory 314, program module 340, program data 342, application programs 338, and an operating system 336. Auditory and visual messages are controlled by the CPU 312, program module 340 and program data 342. In addition to the auditory and visual messages generated by the renal therapy device 104a related to renal therapy being applied to the patient and patient physiological parameters being processed, it is contemplated that the renal therapy device 104a is configured for programming in such a manner that permits auditory and visual messages relating to a plurality of physiological health factors, including heart rate, fluid retention, weight and neuro-hormonal data.

Communication of the renal therapy device 104a with the host system 112 occurs automatically, pursuant to a previously programmed transmission of data interval or an inquiry from the host system 112. Communication of the renal therapy device 104a with the host system 112 may also be prompted by the user of the renal therapy device 104a by engaging a download button. The communication with the host system 112 of the renal therapy device 104a allows the patient or caregiver to review patient renal therapy data along with patient physiological data related to the human body and specific heart functions and implanted CRM device data. When such communications occur automatically in real-time and from a historical perspective it allows the caregiver to review patient renal therapy data along with patient physiological data related to the human body and specific heart functions and CRM device data. The renal therapy device 104a may communicate with the host system 112 via an Internet connection, telephone or satellite transmission or other communication means. Upon a caregiver's review of patient physiological data related to the human body and specific heart functions and implanted cardiac device data following application of renal therapy, the caregiver can determine if changes in the patient renal therapy is necessary in view of the patient physiological data. If it is determined by the caregiver that the patient renal therapy needs to be modified in view of the patient data analyzed, the revised patient renal therapy may be programmed by the caregiver into the host system 112. The host system may then, upon instruction of the caregiver or other scheduled update times, transmit to the renal therapy device 104*a*, and the patient the revised renal therapy regimen. The revised renal therapy regimen may include data representative of new schedule for dialysis or ultrafiltration along with a prescription and prescription consumption schedule.

It is contemplated that all embodiments of the renal therapy device 104*a* include an over use module as part of the program data 342. The over use module equips the renal therapy device 104*a* with the ability to prevent over uses of the device. The renal therapy device 104*a* is configured and controlled by the program data 342 to prevent inappropriate performance of dialysis and ultrafiltration until the scheduled time for renal therapy. The over use module as well as other aspects of the renal therapy device 104*a* communicates with the host 112 system to communicate inappropriate use of the renal therapy device 104*a* so that the caregiver may take steps to intervene and instruct the patient accordingly.

Figure 5:
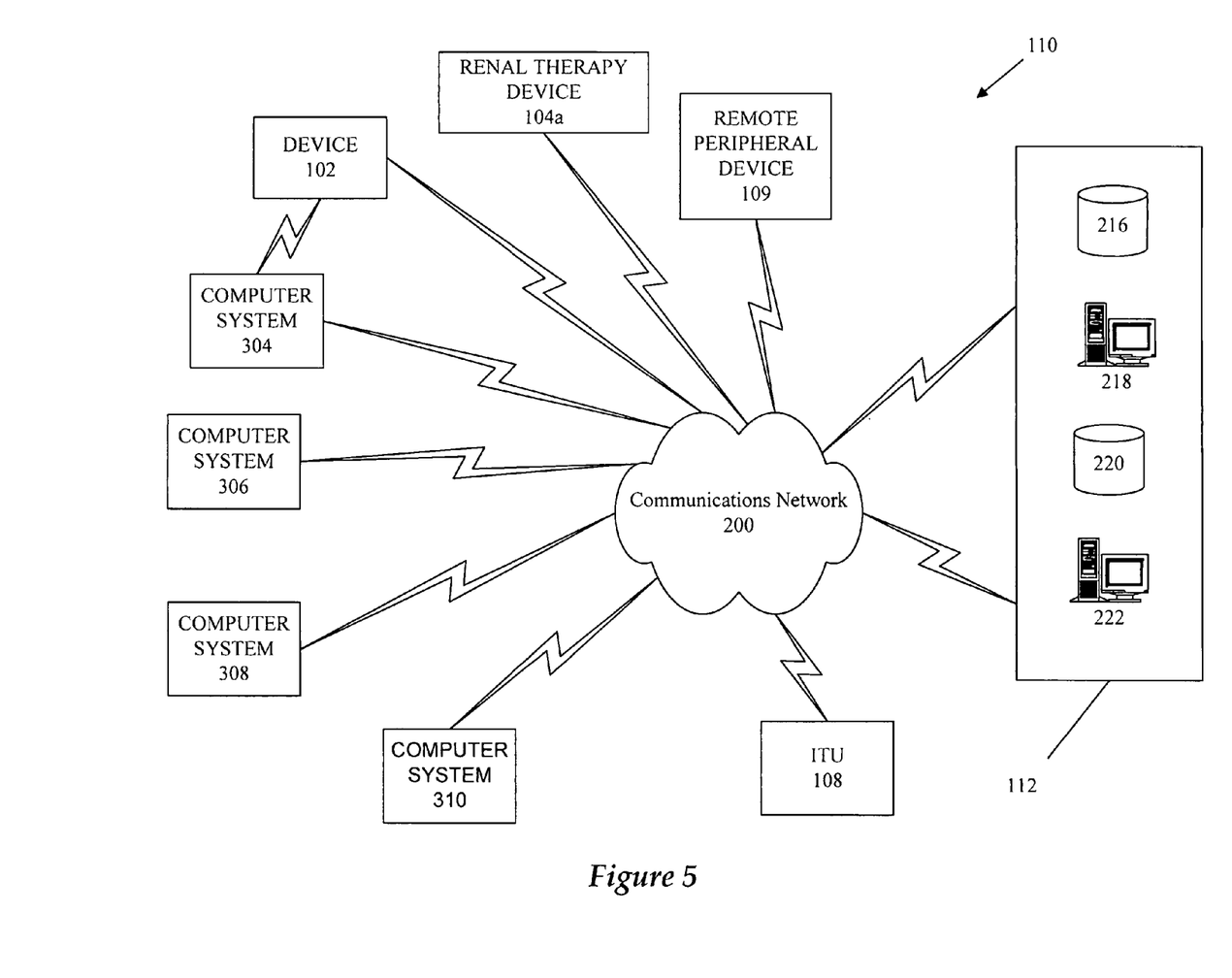
FIG. 5 illustrates an example communication system made in accordance with the present invention.

In the embodiment illustrated in FIG. 5, it is contemplated that the renal therapy device 104*a* is a standalone device. It may be configured to record data and store trending data in device data storage 323 for transmission to a monitor 352 for immediate display. The monitor 352 may be a part of the renal therapy device 104*a* or a separate device configured for electronic connection to the device. In the preferred embodiment, renal therapy device 104*a* is configured to transmit and accept RF telemetry. This configuration provides for the transmission of patient physiological data and renal therapy data between the renal therapy device 104*a* and the implanted CRM device 102*a*. The implanted CRM device 102*a* is configured to transmit patient physiological parameters and to receive renal therapy data transmissions. The implanted CRM device 102*a* stores the data received in implanted device data storage. The data received from the renal therapy device 104*a* and stored by the implanted CRM device 102*a* is transmitted to the host system 112 or a programmer along with all other data stored in implanted device data storage for transmission to the host system 112 by the implanted cardiac rhythmic device 102*a*.

It is further contemplated that the implanted CRM device 102*a* is configured to transmit communications to the renal therapy device 104*a*. In the preferred embodiment, such communications occur via RF transmissions then. Under circumstances where the implanted CRM 102*a* records patient data outside prescribed limits, or determines based on implanted device processing of implanted device data readings that the patient's condition has reached a status requiring urgent changes to the renal therapy (e.g. reducing blood pump speed), the implanted cardiac rhythmic device 102*a* transmits a signal to the renal therapy device 104*a* to initiate an emergency indicator which is designed to instruct the patient or caregiver to immediately modify the therapy. Alternatively the renal therapy device 104*a* could automatically change the therapy and request immediate attention through an alarm.

The advanced patient management system 100 may also include one or more remote peripheral devices 109. The remote peripheral device 109 may include, for example and without limitation, cellular telephones, pagers, PDA devices, facsimiles, remote computers, printers, video and/or audio devices, etc. The remote peripheral device 109 can communicate using wired or wireless technologies and may be used by the patient or caregiver to communicate with the communication system 110 and/or the host 112. For example, the remote peripheral device 109 can be used by the caregiver to receive alerts from the host 112 based on data collected from the patient and to send instructions from the caregiver to either the patient or other clinical staff. In another example, the remote peripheral device 109 is used by the patient to receive periodic or real time updates and alerts regarding the patient's health and well being.

III. Communication System

Communication system 110 provides for communications between and among the various components of the advanced patient management system 100, such as the devices 102, 104, and 106, host 112, and remote peripheral device 109. FIG. 5 illustrates one embodiment for the communication system 110 made in accordance with the present invention. The communication system 110 includes a plurality of computer systems 304, 306, 308, and 310, as well as device 102, host 112, and remote peripheral device 109, connected to one another by the communications network 200. The communications network 200 may be, for example, a local area network (LAN), wide area network (WAN), or the Internet. Communications among the various components, as described more fully below, may be implemented using wired or wireless technologies.

In the example embodiment illustrated in FIG. 5, the host 112 includes server computers 218 and 222 that communicate with computers 304, 306, 308, and 310 using a variety of communications protocols, described more fully below. The server computers 218 and 222 store information in databases 216 and 220. This information may also be stored in a distributed manner across one or more additional servers.

A variety of communication methods and protocols may be used to facilitate communication between devices 102, 104, and 106, ITU 108, communication system 110, host 112, and remote peripheral device 109. For example, wired and wireless communications methods may be used between devices that are not implanted. Only wireless communications are used between implantable devices. Wired communication methods may include, for example and without limitation, traditional copper-line communications such as DSL, broadband technologies such as ISDN and cable modems, and fiber optics, while wireless communications may include, without limitation, cellular, satellite, radio frequency (RF), infrared, ultrasound etc.

For any given communication method, a multitude of standard and/or proprietary communication protocols may be used. For example and without limitation, protocols such as radio frequency pulse coding, spread spectrum, direct sequence, time-hopping, frequency hopping, SMTP, FTP, and TCP/IP may be used. Other proprietary methods and protocols may also be used. Further, a combination of two or more of the communication methods and protocols may also be used. Encryption may also be used to help protect patients' sensitive information.

The various communications between the components of the advanced patient management system 100 may be made secure using several different techniques. For example, encryption and/or tunneling techniques may be used to protect data transmissions. Alternatively, a priority data exchange format and interface that are kept confidential may also be used. Authentication can be implemented using, for example, digital signatures based on a known key structure (e.g., PGP or RSA). Other physical security and authentication measures may also be used, such as security cards and biometric security apparatuses (e.g., retina scans, iris scans, fingerprint scans, veinprint scans, voice, facial geometry recognition, etc.). Conventional security methods such as firewalls may be used to protect information residing on one or more of the storage media of the advanced patient management system 100. Encryption, authentication and/or verification techniques may also be used to detect and correct data transmission errors.

Communications among the various components of the advanced patient management system 100 may be enhanced using compression techniques to allow large amounts of data to be transmitted efficiently. For example, the devices 102, 104, and 106 or the ITU 108 may compress the recorded information prior to transmitting the information to the ITU 108 or directly to the communication system 110.

The communication methods and protocols described above can facilitate periodic and/or real-time delivery of data.

IV. Host

The example host 112 includes a database module 114, an analysis module 116, a medicine module 120, and a delivery module 118 (see FIG. 1). Host 112 preferably includes enough processing power to analyze and process large amounts of data collected from each patient, as well as to process statistics and perform analysis for large populations. For example, the host 112 may include a mainframe computer or multi-processor workstation. The host 112 may also include one or more personal computer systems containing sufficient computing power and memory. The host 112 may include storage medium (e.g., hard disks, optical data storage devices, etc.) sufficient to store the massive amount of high-resolution data that is collected from the patients and analyzed.

The host 112 may also include identification and contact information (e.g., IP addresses, telephone numbers, or a product serial number) for the various devices communicating with it, such as ITU 108 and peripheral device 109. For example, each ITU 108 is assigned a hard-coded or static identifier (e.g., IP address, telephone number, etc.), which allows the host 112 to identify which patient's information the host 112 is receiving at a given instant. Alternatively, each device 102, 104, and 106 may be assigned a unique identification number, or a unique patient identification number (e.g. serial number) may be transmitted with each transmission of patient data.

When a device is first activated, several methods may be used to associate data received by the advanced patient management system 100 with a given patient. For example, each device may include a unique identification number and a registration form that is filled out by the patient, caregiver, or field representative. The registration form can be used to collect the necessary information to associate collected data with the patient. Alternatively, the user can logon to a web site to allow for the registration information to be collected. In another embodiment, a barcode is included on each device that is scanned prior to or in conjunction deployment of the device to provide the information necessary to associate the recorded data with the given patient.

Referring again to FIG. 1, the example database module 114 includes a patient database 400, a population database 402, a medical database 404, and a general database 406, all of which are described further below.

The patient database 400 includes patient specific data, including data acquired by the devices 102a, 104a, and 106a. The patient database 400 also includes a patient's medical records. The patient database 400 can include historical information regarding the devices 102a, 104a, and 106a. For example, if device 102a is an implantable cardioverter defibrillator (ICD), the patient database 400 records the following device information: P and R measurements, pacing frequency, pacing thresholds, shocking events, recharge time, lead impedance, battery voltage/remaining life, ATR episode and EGMs, histogram information, and other device-specific information. In addition, if device 106a is a patient weight scale, the patient database 400 records the patients weight during renal therapy or other prescribed times. The database 400 could also store renal therapy parameters such as frequency of therapy, blood flow, dialysate flow (if applicable), ultrafiltration rate, dialyzer clearance, ultrafiltrate/dialysate conductivity, hematocrit pre- and post-therapy etc. The information stored in the database 400 can be recorded at various times depending on the patient requirements or device requirements. For example, the patient database 400 is updated at periodic intervals that coincide with the patient downloading data from the device. Alternatively, data in the patient database 400 can be updated in real time. Typically, the sampling frequency depends on the health condition of the patient(s) being monitored and the co-morbidities.

The population database 402 includes non-patient specific data, such as data relating to other patients and population trends (e.g. the USRDS database for renal patients or the ADHERE database for decompensated congestive heart failure patients). The population database 402 also records epidemic-class device statistics and patient statistics. The population database 402 also includes data relating to staffing by health care providers, environmental data, pharmaceuticals, etc.

The example medical database 404 includes clinical data relating to the treatment of diseases. For example, the medical database 404 includes historical trend data for multiple patients in the form of a record of progression of their disease (s) along with markers of key events.

The general database 406 includes non-medical data of interest to the patient. This can include, without limitation, information relating to news, finances, shopping, technology, entertainment, and/or sports. The general database 406 can be customized to provide general information of specific interest to the patient. For example, stock information can be presented along with the latest health information as detected from the devices 102, 104, and 106.

In another embodiment, information is also provided from an external source, such as external database 600. For example, the external database 600 includes external medical records maintained by a third party, such as drug prescription records maintained by a pharmacy, providing information regarding the type of drugs that have been prescribed for a patient. This information can be used to alert the caregiver of possible dangerous drug interactions.

The example analysis module 116 includes a patient analysis module 500, device analysis module 502, population analysis module 504, and learning module 506. Patient analysis module 500 may utilize information collected by the advanced patient management system 100, as well as information for other relevant sources, to analyze data related to a patient and provide timely and predictive assessments of the patient's well-being. In performing this analysis, the patient device module 500 may utilize data collected from a variety of sources, include patient specific physiological and subjective data collected by the advanced patient management system 100, medical and historical records (e.g., lab test results, histories of illnesses, etc., drugs currently and previously administered, etc.), as well as information related to population trends provided from sources external to the advanced patient management system 100.

For example, in one embodiment, the patient analysis module 500 makes a predictive diagnosis of an oncoming event based on information stored in the database module 114. For example, the data continuously gathered from a device of a given patient at a heightened risk for a chronic disease event (such as decompensations in heart failure) is analyzed. Based on this analysis, therapy, typically device-based or pharmaceutical, is then applied to the patient either through the device or through clinician intervention. Also data from implanted or external sensors between renal therapies may be used to determine fluid increase in the patient and be used to prescribe renal therapies customized to each patient. For example if the patient does not adhere to a low sodium diet and increases fluid intake, the renal therapy may be prescribed earlier than the scheduled therapy.

In another example embodiment, the patient analysis module 500 provides a diagnosis of patient health status and predicted trend based on present and recent historical data collected from a device as interpreted by a system of expert knowledge derived from working practices within clinics. For example, the patient analysis module 500 performs probabilistic calculations using currently collected information combined with regularly collected historical information to predict patient health degradation.

In another example embodiment, the patient analysis module 500 may conduct pre-evaluation of the incoming data stream combined with patient historical information and information from patients with similar disease states. The pre-evaluation system is based on data derived from working clinical practices and the records of outcomes. The derived data is processed in a neural network, fuzzy logic system, or equivalent system to reflect the clinical practice. Further, the patient analysis module 500 may also provide means for periodic processing of present and historical data to yield a multidimensional health state indication along with disease trend prediction, next phase of disease progression, co-morbidities, and inferences about what other possible diseases may be involved. The patient analysis module 500 may also integrate data collected from internal and external devices with subjective data to optimize management of overall patient health.

Device analysis module 502 analyzes data from the devices 102, 104, and 106 and ITU 108 to predict and determine device issues or failures. For example, if an implanted device 102 fails to communicate at an expected time, device analysis module 502 determines the source of the failure and takes action to restore the performance of the device 102. The device analysis module 502 may also perform additional deterministic and probabilistic calculations. For example, the device analysis module 502 gathers data related to charge levels within a given device, such as an implanted cardiac rhythmic device 102a, and provides analysis and alerting functions based on this information if, for example, the charge level reaches a point at which replacement of the device and/or battery is necessary. Similarly, early degradation or imminent failure of implanted devices can be identified and proactively addressed, or at-risk devices can be closely monitored.

Population analysis module 504 uses the data collected in the database module 114 to manage the health of a population. For example, a clinic managing cardiac patients can access the advanced patient management system 100 and thereby obtain device-supplied advance information to predict and optimize resource allocation both as to immediate care and as a predictive metric for future need of practicing specialists. As another example, the spread of disease in populations can be localized and quarantined, as needed, rapidly before further spreading or an outbreak ensues.

In one embodiment, population analysis module 504 trends the patient population therapy and management as recorded by the devices and directs health care resources to best satisfy the needs of the population. The resources can include people, facilities, supplies, and/or pharmaceuticals. In other embodiments, the population analysis module detects epidemics and other events that affect large population groups. The population analysis module 504 can issue alerts that can initiate a population quarantine, redirect resources to balance size of staffing with population demand, and predict possible future need of qualified specialists.

The population analysis module 504 may utilize a variety of characteristics to identify like-situated patients, including but not limited to, sex, age, genetic makeup, etc. The population analysis module 504 may develop large amounts of data related to a given population based on the information collected by the advanced patient management system 100. In addition, the population analysis module 504 may integrate information from a variety of other sources. For example, the population analysis module 504 may utilize data from public domain databases (e.g., the National Institute of Health), public and governmental and health agency databases, private insurance companies, medical societies (e.g., the American Heart Association), and genomic records (e.g., DNA sequences).

In one embodiment of the invention, the host 112 may be used as a "data clearinghouse," to gather and integrate data collected from the devices 102, 104, and 106, as well as data from sources outside the advanced patient management system 100. The integrated data can be shared with other interested entities, subject to privacy restrictions, thereby increasing the quality and integration of data available.

Learning module 506 analyzes the data provided from the various information sources, including the data collected by the advanced patient system 100 and external information sources. For example, the learning module 506 analyzes historical symptoms, diagnoses, and outcomes along with time development of the diseases and co-morbidities. The learning module 506 can be implemented via a neural network (or equivalent) system.

The learning module 506 can be partially trained (i.e., the learning module 506 may be implemented with a given set of preset values and then learn as the advanced patient management system functions) or untrained (i.e., the learning module 506 is initiated with no preset values and must learn from scratch as the advanced patient management system functions). In other alternative embodiments, the learning module 506 may continue to learn and adjust as the advanced patient management system functions (i.e., in real time), or the learning module 506 may remain at a given level of learning and only advanced to a higher level of understanding when manually allowed to do so.

In a neural network embodiment, new clinical information is presented to create new neural network coefficients that are distributed as a neural network knowledge upgrade. The learning module 506 can include a module for verifying the neural network conclusions for clinical accuracy and significance. The learning module can analyze a database of test cases, appropriate outcomes and relative occurrence of misidentification of the proper outcomes. In some embodiments, the learning module 506 can update the analysis module 116 when the analysis algorithms exceed a threshold level of acceptable misidentifications.

The example-learning module 506 uses various algorithms and mathematical modeling including, but not limited to, trend and statistical analysis, data mining, pattern recognition, cluster analysis, neural networks and fuzzy logic. Learning module 506 may perform deterministic and probabilistic calculations. Deterministic calculations include algorithms for which a clear correlation is known between the data analyzed and a given outcome. For example, there may be a clear correlation between the energy left in a battery of an implantable device and the amount of time left before the battery must be replaced.

A probabilistic calculation involves the correlation between data and a given outcome that is less than 100% certain. Probabilistic determinations require an analysis of several possible outcomes and an assignment of probabilities for those outcomes (e.g., an increase in weight of a patient may, at a 25% probability, signal an impending de-compensation event and/or indicate that other tests are needed). The learning module 506 performs probabilistic calculations and selects a given response based on less than a 100% probability. Further, as the learning module 506 "learns" from previous determinations (e.g., through a neural network configuration), the learning module 506 becomes more proficient at assigning probabilities for a given data pattern, thereby being able to more confidently select a given response. As the amount of data that has been analyzed by the learning module 506 grows, the learning module 506 becomes more and more accurate at assigning probabilities based on data patterns. A bifurcated analysis may be performed for diseases exhibiting similar symptoms. As progressive quantities of data are collected and the understanding of a given disease state advances, disease analysis is refined where a former singular classification may split into two or more sub-classes.

In addition, patient-specific clinical information can be stored and tracked for hundreds of thousands of individual patients, enabling a first-level electronic clinical analysis of the patient's clinical status and an intelligent estimate of the patient's short-term clinical prognosis. The learning module 506 is capable of tracking and forecasting a patient's clinical status with increasing levels of sophistication by measuring a number of interacting co-morbidities, all of which may serve individually or collectively to degrade the patient's health. This enables learning module 506, as well as caregivers, to formulate a predictive medical response to oncoming acute events in the treatment of patients with chronic diseases such as heart failure, diabetes, pain, cancer, and asthma/COPD, as well as possibly head-off acute catastrophic conditions such as a stroke.

Delivery module 118 coordinates the delivery of feedback based on the analysis performed by the host 112. In response to the analysis module 116, delivery module 118 can manage the devices 102, 104, and 106, perform diagnostic data recovery, program the devices, and otherwise deliver information as needed. In some embodiments, the delivery module 118 can manage a web interface that can be accessed by patients or caregivers. The information gathered by an implanted device can be periodically transmitted to a web site that is securely accessible to the caregiver and/or patient in a timely manner. In other embodiments, a patient accesses detailed health information with diagnostic recommendations based upon analysis algorithms derived from leading health care institutions.

For example, the caregiver and/or patient can access the data and analysis performed on the data by accessing one or more general content providers. In one example, the patient's health information is accessed through a general portal such as My Yahoo provided by Yahoo! Inc. of Sunnyvale, Calif. A patient can access his or her My Yahoo homepage and receive information regarding current health and trends derived from the information gathered from the devices 102, 104, and 106, as well as other health information gathered from other sources. The patient may also access other information in addition to health information on the My Yahoo website, such as weather and stock market information. Other electronic delivery methods such as email, facsimile, etc. can also be used for alert distribution.

In an alternative embodiment, the data collected and integrated by the advanced patient system 100, as well as any analysis performed by the patient management system 100, is delivered by delivery module 118 to a caregiver's hospital computer system for access by the caregiver. A standard or custom interface facilitates communication between the advanced patient management system 100 and a legacy hospital system used by the caregiver so that the caregiver can access all relevant information using a system familiar to the caregiver.

The advanced patient management system 100 can also be configured so that various components of the system (e.g., ITU 108, communication system 110, and/or host 112) provide reporting to various individuals (e.g., patient and/or caregiver). For example, different levels of reporting can be provided by (1) the ITU 108 and (2) the host 112. The ITU 108 may be configured to conduct rudimentary analysis of data gathered from devices 102, 104, and 106, and provide reporting should an acute situation be identified. For example, if the ITU 108 detects that a significant heart arrhythmia is imminent or currently taking place, the ITU 108 provides reporting to the patient in the form of an audible or visual alarm.

The host 112 can provide a more sophisticated reporting system. For example, the host 112 can provide exception-based reporting and alerts that categorize different reporting events based on importance. Some reporting events do not require caregiver intervention and therefore can be reported automatically. In other escalating situations, caregiver and/or emergency response personnel need to become involved. For example, based on the data collected by the advanced patient management system 100, the delivery module 118 can communicate directly with the devices 102, 104, and 106, contact a pharmacy to order a specific medication for the patient, and/or contact 911 emergency response. In an alternative embodiment, the delivery module 118 and/or the patient may also establish a voice communication link between the patient and a caregiver, if warranted.

In addition to forms of reporting including visual and/or audible information, the advanced patient management system 100 can also communicate with and reconfigure one or more of the devices 102, 104, and 106. For example, if device 102 is part of a CRM system, the host 112 can communicate with the device 102 and reconfigure the therapy provided by the CRM system based on the data collected from one or more of the devices 102, 104, and 106. In another embodiment, the delivery module 118 can provide to the ITU 108 recorded data, an ideal range for the data, a conclusion based on the recorded data, and a recommended course of action. This information can be displayed on the ITU 108 for the patient to review or made available on the peripheral device 109 for the patient and/or clinician to review.

One or more headings have been provided above to assist in describing the various embodiments disclosed herein. The use of headings, and the resulting division of the description by the headings, should not be construed as limiting in any way. The subject matter described under one heading can be combined with subject matter described under one or more of the other headings without limitation and as desired.

The systems and methods of the present disclosure can be implemented using a system as shown in the various figures disclosed herein including various devices and/or programmers, including implantable or external devices. Accordingly, the methods of the present disclosure can be implemented: (1) as a sequence of computer implemented steps running on the system; and (2) as interconnected modules within the system. The implementation is a matter of choice dependent on the performance requirements of the system implementing the method of the present disclosure and the components selected by or utilized by the users of the method. Accordingly, the logical operations making up the embodiments of the method of the present disclosure described herein can be referred to variously as operations, steps, or modules. It will be recognized by one of ordinary skill in the art that the operations, steps, and modules may be implemented in software, in firmware, in special purpose digital logic, analog circuits, and any combination thereof without deviating from the spirit and scope of the present invention as recited within the claims attached hereto.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

I claim:

1. An integrated cardiorenal disease therapy management system, comprising:
   a. a renal therapy device including at least one of an external dialysis device or an external ultrafiltration device configured to provide renal therapy to a subject;
   b. an implantable cardiac rhythm management device including:
      a sensor for measuring data representative of a patient physiological parameter; and
      a cardiac rhythm management therapy circuit configured to provide cardiac rhythm management therapy to the subject; and
   c. a control system coupled to the renal therapy device and configured to receive the data representative of the patient physiological parameter, wherein the control system directs therapy provided by the renal therapy device using information from the data representative of the patient physiological parameter received from the implantable cardiac rhythm management device when the implantable cardiac rhythm management device has been implanted in the subject.

2. The cardiorenal disease therapy management system of claim 1 wherein the control system directs therapy, provided by the renal therapy device, using information from the data representative of the patient physiological parameter received from the implantable cardiac rhythm management device when the implantable cardiac rhythm management device has been implanted in the subject, by modifying at least one of the following: flow of blood through the renal therapy device, flow of dialysate or ultrafiltrate through the renal therapy device, flow of a medication or saline into the renal therapy device, ionic composition of dialysate fluid flowing into the renal therapy device, or temperature of blood or dialysate in the renal therapy device.

3. The cardiorenal disease therapy management system of claim 1 wherein the renal therapy device is a dialysis therapy device.

4. The cardiorenal disease therapy management system of claim 1 wherein the renal therapy device is an ultrafiltration therapy device.

5. The cardiorenal disease therapy management system of claim 1 wherein the patient physiological parameter comprises data representative of at least one of the following: heart rate, heart rate variability, electrogram, autonomic balance, heart vibrations, thoracic impedance, thoracic fluid status, intracardiac pressure, cardiac oxygenation, patient activity level, patient temperature, blood pressure, breathing pattern, blood chemistry, pH, blood conductivity, blood flow, blood oxygenation, cardiac volume, cardiac output, ejection fraction, or stroke volume.

6. The cardiorenal disease therapy management system of claim 1 wherein the control system directs therapy by modifying flow of a medication or saline into the renal therapy device.

7. The cardiorenal disease therapy management system of claim 1 wherein the control system directs therapy by modifying an ionic composition of dialysate fluid flowing into the renal therapy device.

8. The cardiorenal disease therapy management system of claim 1 wherein the control system directs therapy by modifying a temperature of blood or dialysate in the renal therapy device.

9. The cardiorenal disease therapy management system of claim 1 wherein the patient physiological parameter comprises data representative of autonomic balance.

10. The cardiorenal disease therapy management system of claim 1 wherein the patient physiological parameter comprises data representative of patient activity level.

11. The cardiorenal disease therapy management system of claim 1 wherein the patient physiological parameter comprises data representative of patient temperature.

12. The cardiorenal disease therapy management system of claim 1 wherein the patient physiological parameter comprises data representative of a breathing pattern.

13. The cardiorenal disease therapy management system of claim 1 wherein the patient physiological parameter comprises data representative of blood chemistry.

14. The cardiorenal disease therapy management system of claim 1, wherein the control system is configured to provide an alarm indication when the patient physiological parameter exceeds a specified threshold.

15. A method of controlling renal therapy delivered to a patient from an external renal therapy device, the method comprising:
   a. transmitting data representative of a patient physiological parameter from at least one sensor of a cardiac rhythm management device implanted in the patient and configured to provide cardiac rhythm management therapy comprising at least one of pacing, anti-tachyarrhythmia, or cardiac resynchronization therapy to the patient;
   b. processing the data; and
   c. modifying the renal therapy delivered to the patient using information from the data representative of the patient physiological parameter received from the cardiac rhythm management device implanted within the patient and configured to provide the cardiac rhythm management therapy to the patient.

16. The method of claim 15 wherein the renal therapy comprises ultrafiltration and the renal therapy device comprises an ultrafiltration device.

17. The method of claim 16 including trending the patient physiological parameter to determine a cardiovascular performance change in relation to an ultrafiltration rate, wherein the data representative of the patient physiological parameter includes at least one of thoracic fluid status, cardiac volume, blood conductivity, or heart rate variability received from the cardiac rhythm management device implanted within the patient and configured to provide the cardiac rhythm management therapy to the patient.

18. The method of claim 15 wherein the processing further comprises processing data representative of a blood pressure of the patient, and wherein the modifying further comprises modifying a rate at which blood is removed from the patient's body in response to the data representative of the blood pressure of the patient, received from the cardiac rhythm management device implanted within the patient and configured to provide the cardiac rhythm management therapy to the patient.

19. The method of claim 15 wherein the processing further comprises processing data representative of a transthoracic impedance of the patient, wherein the data representative of the transthoracic impedance of the patient includes an indication of the patient's thoracic fluid status, and wherein the modifying further comprises modifying fluid removal from the patient's body in response to the data representative of the transthoracic impedance of the patient received from the cardiac rhythm management device implanted within the patient and configured to provide the cardiac rhythm management therapy to the patient.

20. The method of claim 15 further including measuring a fluid volume within the patient using the implanted cardiac rhythm management device and transmitting from the implanted cardiac rhythm management device data representative of the fluid volume to control in real-time the renal therapy the patient receives.

21. The method of claim 15, wherein the renal therapy comprises at least one of the following therapies: dialysis therapy or ultrafiltration therapy.

22. A renal disease therapy management system, comprising:
   a. a renal therapy device including at least one of an external dialysis device or an external ultrafiltration device configured to provide renal therapy to a subject;
   b. an implantable cardiac rhythm management device including:
      a sensor for data representative of a patient physiological parameter; and
      a cardiac rhythm management therapy circuit configured to provide cardiac rhythm management therapy to the subject;
   c. a control system coupled to the renal therapy device and configured to receive the data representative of the patient physiological parameter, wherein the control system directs therapy provided by the renal therapy device using information from the data representative of the patient physiological parameter received from the implantable cardiac rhythm management device when the implantable cardiac rhythm management device has been implanted in the subject; and
   d. a health management host system coupled to the renal therapy device and the implantable cardiac rhythm management device in a manner that allows data transmission between the implantable cardiac rhythm management device and the renal therapy device when the implantable cardiac rhythm management device has been implanted in the subject.

23. The renal disease therapy management system of claim 22, wherein the health management host system is configured to analyze and display renal therapy data and data representative of a patient physiological parameter on a health management display.

24. The renal disease therapy management system of claim 23, wherein the patient physiological data includes fluid retention data.

25. The renal disease therapy management system of claim 23, wherein the renal therapy device is configured with a display device to illustrate a renal therapy strategy.

26. The renal disease therapy management system of claim 22, wherein the renal therapy device comprises a dialysis machine.

27. The renal disease therapy management system of claim 22, wherein the renal therapy device comprises an ultrafiltration machine.

* * * * *